United States Patent [19]
Watson et al.

[11] Patent Number: 6,063,541
[45] Date of Patent: *May 16, 2000

[54] HYDRAZIDES

[75] Inventors: Richmond C. Watson; Albert B. Levit; Rolf S. Gabrielsen, all of Binghamton; Bruce M. Resnick, Vestal, all of N.Y.

[73] Assignee: Kodak Polychrome Graphics LLC, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/778,468

[22] Filed: Jan. 3, 1997

Related U.S. Application Data

[60] Provisional application No. 60/009,724, Jan. 5, 1996.
[51] Int. Cl.$^7$ ....................................................... G03C 1/06
[52] U.S. Cl. ............................................ 430/264; 564/310
[58] Field of Search ..................................... 430/264, 566; 564/310

[56] References Cited

U.S. PATENT DOCUMENTS

| | | | |
|---|---|---|---|
| 4,994,365 | 2/1991 | Looker et al. | 430/264 |
| 5,126,227 | 6/1992 | Machoukin et al. | 430/264 |
| 5,316,890 | 5/1994 | Okamura et al. | 430/264 |

FOREIGN PATENT DOCUMENTS

| | | |
|---|---|---|
| 5-61144 | 3/1993 | Japan . |
| 5-150392 | 6/1993 | Japan . |
| 6-273879 | 9/1994 | Japan . |
| 8-248556 | 9/1996 | Japan . |

*Primary Examiner*—Hoa Van Le
*Attorney, Agent, or Firm*—Ratner & Prestia

[57] ABSTRACT

This subject invention relates to novel hydrazide compounds useful as dot-promoting agents in photographic image systems, methods for making them, and to photographic materials which comprise these compounds.

17 Claims, No Drawings

HYDRAZIDES

This application claims priority pursuant to 35 U.S.C. 119 from U.S. provisional application Ser. No. 60/009,724 filed Jan. 5, 1996, the entire disclosure of which is hereby incorporated by reference.

FIELD OF THE INVENTION

The subject invention relates to novel hydrazide compounds useful as dot-promoting agents in photographic image systems, to methods for making them, and to photographic materials which comprise these compounds.

DESCRIPTION OF THE PRIOR ART

Traditionally, the production of high quality halftone dots was obtained with the use of "lith" films and chemistry. These films, used for making halftone and line images were capable of producing extremely high contrast and good image sharpness. Sharpness is quantified in terms of "edge gradient" which is the ratio of change in optical density (Δ) to distance at the boundary between the exposed part and the unexposed part of the photographic image: In general, the higher the edge gradient the sharper the image, e.g., the harder the dot. In the case of halftone images such properties contribute to "hard dot quality".

Those skilled in the art attribute the formation of hard dots produced with lith materials to the high contrast obtained from "infectious development" as described by Yule, J., Frank. Inst., 239; 221, (1945). In fact high contrast has come to be synonymous with high edge gradient.

Although the dot quality delivered from lith materials is excellent, the lith system has serious disadvantages which restrict its utility. As has been recognized, the disadvantages of the lith system include a shortened useful life of the processing chemistry and deterioration of the image quality due to pepper spots, drag streaks, narrow screen range and high dependence on processing.

As an alternative to the lith system, soluble hydrazides have been incorporated into photographic elements for the purpose of creating high contrast images. However, it is preferred that their mobility is reduced. Typically, this can be achieved by incorporating either a ballast group or a functionality that promotes adsorption to the surface of the silver halide grain. The selection of an adsorption-promoting substituent for a phenyl hydrazide is limited however, in that "tightly adsorbed aryl hydrazides are not usually efficient in increasing the contrast in negative-working silver halide emulsions. It is believed that contrast is increased by infectious development and that undue restriction of mobility interferes with the ability of the aryl hydrazides to promote infectious development". Parton, U.S. Pat. No. 4,459,347. The delicate balance necessary to provide adsorptivity to the silver halide grain while still providing adequate solubility, as well as the requirement for chemical stability and inherent activity, place serious constraints upon the design of new aryl hydrazide contrast-enhancing agents.

When groups such as thiourea, thioamide, heterocyclic rings, or urea are used as adsorption-promoting functionalities, the molar concentration of the hydrazide can be reduced by an order of magnitude without loss of activity. This was a significant advantage over the use of mobile (soluble) hydrazides because, at the high concentrations necessary to effect contrast enhancement in a negative emulsion, some hydrazides release sufficient nitrogen to disrupt the ordered array of the photographic element and thereby deteriorate the image quality. Furthermore, diffusion of the mobile hydrazides into the processing chemistry alters the properties of the chemistry with time. The potential generation of nitrogen and the diffusion of hydrazides into the processing chemistry are two factors which have lead to the desire to reduce the concentration of hydrazide to minimum level necessary for suitable development. In addition, another motivating factor in reducing the concentration of the hydrazides is the cost of the hydrazides. The preparation usually involves a multistep synthesis and the hydrazides can be the most expensive component in the photosensitive layer.

Significantly, although both the mobile hydrazides and the hydrazides provided with an adsorption-promoting moiety substantially increase the contrast of a photographic emulsion, only a selected few of the latter class also provide acceptable dot quality. Undoubtedly, the dual constraints described above, on controlled adsorptivity of the hydrazide and the printing demand for long screen range, severely limit the initially large number of choices of hydrazide derivatives that produce high contrast. Therefore, it follows that these constraints also limit the number of hydrazides that can produce high quality dots since high contrast is a necessary (though not sufficient) factor in producing high-quality dots.

Use of certain booster amines has also been disclosed in Looker, U.S. Pat. No. 4,994,365, where ballasted hydrazides have been described having the structure:

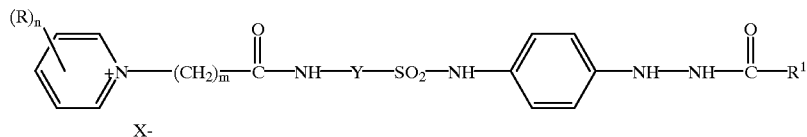

wherein each R is an alkyl group, preferably containing 1 to 12 carbon atoms, n is 1 to 3, X is an anion such as chloride or bromide, m is 1 to 6, Y is a divalent aromatic radical, and $R^1$ is hydrogen or a blocking group. The divalent aromatic radical represented by Y, such as a phenylene radical or naphthalene radical, can be unsubstituted or substituted with one or more substituents such as alkyl, halogen, alkoxy, haloalkyl or alkoxyalkyl. These hydrazides have been combined with amine boosters of well defined structures added to the coating formulation.

While the invention of U.S. Pat. No. 4,994,365 represents an important technical progress it still suffers from the disadvantage of having to rely on the complex balancing of "incorporated boosters" and additional activity regulators to achieve the necessary activity of the system in an operable pH range.

One aspect of eminent practical and commercial value of photographic assemblies of this type is the stability of unprocessed film material under quite adverse conditions. Of equal importance is the reliability and consistent photographic performance of the materials. These aspects favor a simple and flexible design.

A mechanism by which hydrazides operate has been proposed by Okamura et al. East-West IS&T Meeting 1993 and by K. I. Shinohara et al., J. Photo. Sci., 35; 181, 1987, but this proposal should be considered only as a theory by which the present inventive entity is not bound. Based on the proposed mechanism, it becomes quite obvious to those skilled in the art that activity and stability of hydrazides and/or the combination of hydrazides and booster amines are difficult to balance, e.g., the more active a compound or a combination of compounds, the less likely that the compound or combination will exhibit good long term stability.

Sufficient activity and stability are often so tightly interconnected that they seem to be mutually exclusive. Therefore, what is required are hydrazide compounds with improved stability when incorporated into a photographic material and hydrazide compounds which have been optimized with respect to their activity. It is also desirable to keep the systems simple and easy to control. There exists moreover a need for photographic materials, particularly in the field of graphic arts (i.e. in connection with negative-working surface-latent image emulsions), which function in processing systems with high stability under normal working conditions. It has long been recognized that such stable processing solutions, in particular developer solutions, can only be obtained if the pH of such solutions is kept as low as possible, that is in the range of 9.5 to 12.0, preferably in the range of 9.5 to 11.0.

It has been reported (IS & T 46th Annual Conference 1993) that (generally speaking) a major factor in achieving sufficient activity in hydrazide-promoted photographic systems processed at a pH of 10.5 is strictly linked to hydrazide structures where the ballasting group is linked to the aromatic ring connected to the hydrazide via a sulfonamido group. (See Looker, U.S. Pat. No. 4,994,365.)

The present invention also addresses recent advances in pre-press printing operations. Pre-press areas of copy preparation, typesetting, photography, and film assembly involve intricate manual operations which are time consuming, expensive, and require highly skilled craftsmen. These operations have been serious bottlenecks to production, which is why most new developments in the industry have been targeted at the pre-press areas. Efficiencies have improved as image setting equipment has replaced the most conventional means of preparing the negative flats or film positives that are necessary for platemaking. Beside the obvious customer benefit of using smaller quantities of photographic media, the most significant impact to photographic manufacturers and designers is the elimination of the need for a halftone screen to produce the halftone dots that are necessary to convert continuous tone copy to discrete, printable dots.

Recent developments in screening technologies such as "Stochastic Screening" and "High Definition Printing" offer the printer significant advantages not realizable with conventional screening. In first order stochastic screening, small spots 14 to 30 microns, are randomly placed to generate a tone. A 21 micron spot is about the size of a 1% dot in a regular 150-line screen. The smallness and randomness of the dots eliminates objectionable moire patterns which result when regular screens are used to print multicolor images. Additionally, more-detail is carried by a stochastic screen, i.e. calculations show that for a 20% tone a normal 150 line-per-inch (lpi) screen will have 22,500 dots in a 1×1 inch square whereas the stochastic screen will have 14/3 times that number of dots in the same area. The result is more detailed information in the print, and the print appears more like a continuous tone image. In High Definition Printing (HDP) very fine line screens, as fine as 600 lpi, are employed and again very small dots appear in the "highlight" region of the image. This tends to make "rosettes" too small to be seen and any moiré patterns too fine to be observed.

In order to realize the above advantages, image-setting film which can reproduce very small spots with no fringe (fuzziness) and high core microdensity are required. Low core-microdensity will make a dot which cannot be reproduced on plate, and fringe area around dots is objectionable because the amount of the dot fringe which is reproduced on plates is difficult to control. In stochastic screening and HDP applications, the short duration exposures used to generate small dots when combined with the low film gradient in "Rapid Access" films, produces dots having poor core microdensity and a large fringe area. Imagesetter exposure intensities can be increased to improve the core microdensity in the dots, but this increases the objectionable dot fringe area. What is required is a high gradient film which can reproduce very small dots with height core microdensity and no fringe.

High-contrast films tended to suffer from the inability to reproduce the very small dots in the highlight area as well as the larger dots required in the shadow region. This defect is especially noted with high resolution using >150 lpi screen or in stochastic screening. The effect of this shortened screen range is that the reproduction cannot contain all the information found in the original copy.

The present invention is directed to new diffusion-fast hydrazides of high activity and high stability corresponding to structures described in the following summary. The invention is also directed to photographic materials containing such hydrazides.

The present invention is also directed to a method for producing high quality dot images that solves most of the problems inherent in the lith system. The method involves the use of novel hydrazide derivatives as additives to silver halide emulsions for the purpose of providing good dot quality. However, the invention is not limited to lith-type emulsion systems and the present hydrazides can be used for all purposes for which hydrazides or hydrazines have been found to provide an advantage, e.g., in hybrid-type systems in which hydrazides are incorporated in the so-called "rapid access" photographic materials.

OBJECTS OF THE INVENTION

An object of the invention is to provide novel hydrazide compounds which act as contrast-enhancing agents that can be used in photographic assemblies to provide high contrast, i.e., wherein gamma ($\gamma$) will be greater than about 8, negative images and provide sufficient activity without requiring a booster amine, (although a booster amine could be added if desired.)

A further object of the present invention is to provide hydrazides with high activity, i.e. hydrazides which possess the ability to generate negatives having high gradation under low-pH development conditions, and display long-term stability when incorporated into photographic assemblies.

Another object of the present invention is to provide a photographic element that can be processed in a stable developer having a pH<11 and still yielding a high contrast material.

Another object of the present invention is to reduce or minimize the concentration of hydrazide in a photographic element.

Furthermore, it is an object of the present invention to provide a photographic element which exhibits improved speed, minimal pepper, improved development rate, improved line edge or dot quality, and improved screen range on development.

In particular, the presence of these compounds in photographic silver halide material facilitates the process of forming a high contrast image which permits the production of dot and line images possessing high image quality when exposed in graphic arts cameras or when exposed by electronic scanners, film plotters, image setters using lasers or other high intensity light sources for exposure.

SUMMARY OF THE INVENTION

The present invention provides hydrazide compounds having Formula 1:

DETAILED DESCRIPTION

All patents, patent applications, and literature references cited in the specification are hereby incorporated by reference in their entirety. In the case of inconsistencies, the present disclosure, including definitions, will prevail.

The novel hydrazide compounds of the invention are useful as dot-promoting agents in photographic image systems, to methods for making them, and to photographic materials which comprise these compounds. The hydrazides of the invention are useful for improving the quality of photographic reproductions and provide an element having reduced cost, reduced nitrogen generation, and reduced hydrazide diffusion into the processing solution.

X and Y are arylene groups such as, for example, phenyl, naphthyl, tetrahydronaphthyl, and the like. These groups can Formula 1

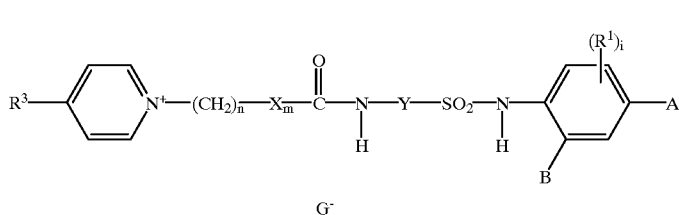

wherein each $R^1$, is independently selected from the group consisting of hydrogen, alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; or two of the $R^1$ groups taken together can form a carbocyclic ring containing 5–10 atoms;

i is from 1 to 3, m is from 0 to 1, and n is from 1 to about 6.

A and B are independently selected from the group consisting of —NHNH—COCO—L—Z , hydrogen, alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; with the proviso that at least one of A and B is a —NHNH—COCO—L—Z group.

L is O, or $NR^2$;

$R^2$ is hydrogen, alkyl, or aralkyl; and

Z is selected from the group consisting of $C_2$–$C_6$alkyl and $C_3$–$C_6$cycloalkyl; wherein the alkyl and cycloalkyl groups are substituted with from 1 to 3 groups selected from hydroxyl, $C_1$–$C_3$hydroxyalkyl, $C_1$–$C_5$ alkoxy, polyethyleneoxy, and any combination of the foregoing.

X and Y are arylene groups which can optionally be substituted.

$R^3$ is alkyl having from about 4 to about 20 carbon atoms or aralkyl having from 6 to about 10 atoms.

G is a monovalent anion. Preferably the anion is selected from bromide, chloride, thiocyanate, tosylate or mesylate.

The present invention also contemplates use of the hydrazides having Formula I in a photographic element (and a photographic element incorporating one or more of said hydrazides) that can be processed in a stable developer having a pH<11 and still yield a high-contrast material. The photographic elements of the invention exhibit improved speed, improved development rate, improved line edge or dot quality, improved screen range, and reduced pepper grain on development. The hydrazide can be incorporated in an emulsion layer or in another hydrophilic colloid layer of the photographic element.

be substituted with one or more substituents. Suitable substituents include groups such as, for example, alkyl, alkoxy, aryl, alkaryl, arylalkyl, hydroxy, amino, halo, sulfonyl, and the like. Preferred substituents include lower alkyl groups such as, for example, methyl, dimethyl, ethyl and the like.

Useful Z groups include, but are not limited to, groups such as, for example, hydroxyethyl, hydroxypropyl, methoxyethyl, dihydroxypropyl, and the like.

Examples of the carbocyclic group formed when two of the $R^1$ groups form a ring include but are not limited to phenyl, naphthyl, cyclopentyl, cyclohexyl, cycloheptyl, cyclooctyl, and the like.

The $R^3$ group is an alkyl ballast group having from about 4 to about 20 carbon atoms or an aralkyl ballast group having from 6 to about 10 carbon atoms. Examples of suitable alkyl ballast groups include, but are not limited to, groups such as, for example, hexyl, heptyl, octyl, nonyl, decyl, undecyl and dodecyl. The $R^3$ can be a straight chain group or it can be a branched group. In addition, the ballast groups can be substituted with groups such as, for example, alkyl, alkoxy, aryl, alkaryl, arylalkyl, hydroxy, amino, halo, sulfonyl, and the like. Preferred substituents are octyl, nonyl, and decyl. Preferred $R^3$ groups are 1-butyl-pentyl or 3-phenyl-n-propylene.

For $R^1$ and $R^2$, without limitation, the alkyl groups can have from 1 to about 20 carbon atoms, the alkenyl groups can have from 2 to about 20 carbon atoms, the cycloalkyl groups can have from 3 to about 20 carbon atoms, and the aryl groups can have from 6 to about 20 carbon atoms. The preferred alkyl groups can have from 1 to about 10 carbon atoms, the preferred alkenyl groups can have from 2 to about 10 carbon atoms, the preferred cycloalkyl groups can have from 3 to about 10 carbon atoms and the preferred aryl groups can have from 6 to about 10 carbon atoms. The most preferred alkyl groups, lower alkyl groups, have from 1 to about 6 carbon atoms. The most preferred alkenyl groups, lower alkenyl groups, have from 2 to about 6 carbon atoms. The most preferred cycloalkyl groups have from 3 to about 6 carbon atoms and the preferred aryl and arylene groups have from 6–10 carbon atoms.

In the compounds of the invention, the preferred cycloalkyl groups have 5, 6, or 7 ring atoms. The most preferred cycloalkyl groups will have 5 or 6 ring atoms.

In general, preferred are compounds within Formula 1 having a hydrophilic-lipophilic balance (HLB) lower than 2.2; further preferred are components within the foregoing formula having HLB lower than 2.

The term "hydrophilic-lipophilic balance," as used herein, refers to the log P value of the compound with respect to the system n-octanol/water as defined by the equation:

$$\text{Log} P = \log([X]_{octanol}/[X]_{water})$$

where X=concentration of the compound. The partition coefficient is a measure of the ability of a compound to partition between aqueous and organic phases and is calculated in the manner described in an article by A. Leo, P. Y. C. Jow, C. Silipo and C. Hansch, *Journal of Medicinal Chemistry*, Vol. 18, No. 9, pp. 865–868, 1975. Calculations for log P can be carried out using Clog P for Windows, Version 1.0.0, Biobyte Corporation, 201 West 4th Street, Claremont, Calif. 91711. The higher the value of log P the more hydrophobic the compound. Compounds with a log P of greater than zero are hydrophobic, i.e., they are more soluble in organic media than in aqueous media, whereas compounds with a log P of less than zero are hydrophilic. A compound with a log P of one is ten times more soluble in organic media than in aqueous media and a compound with a log P of two is one hundred times more soluble in organic media than in aqueous media.

Specific examples of compounds represented by the general formula 1 are given below. However, present invention is not limited to these examples.

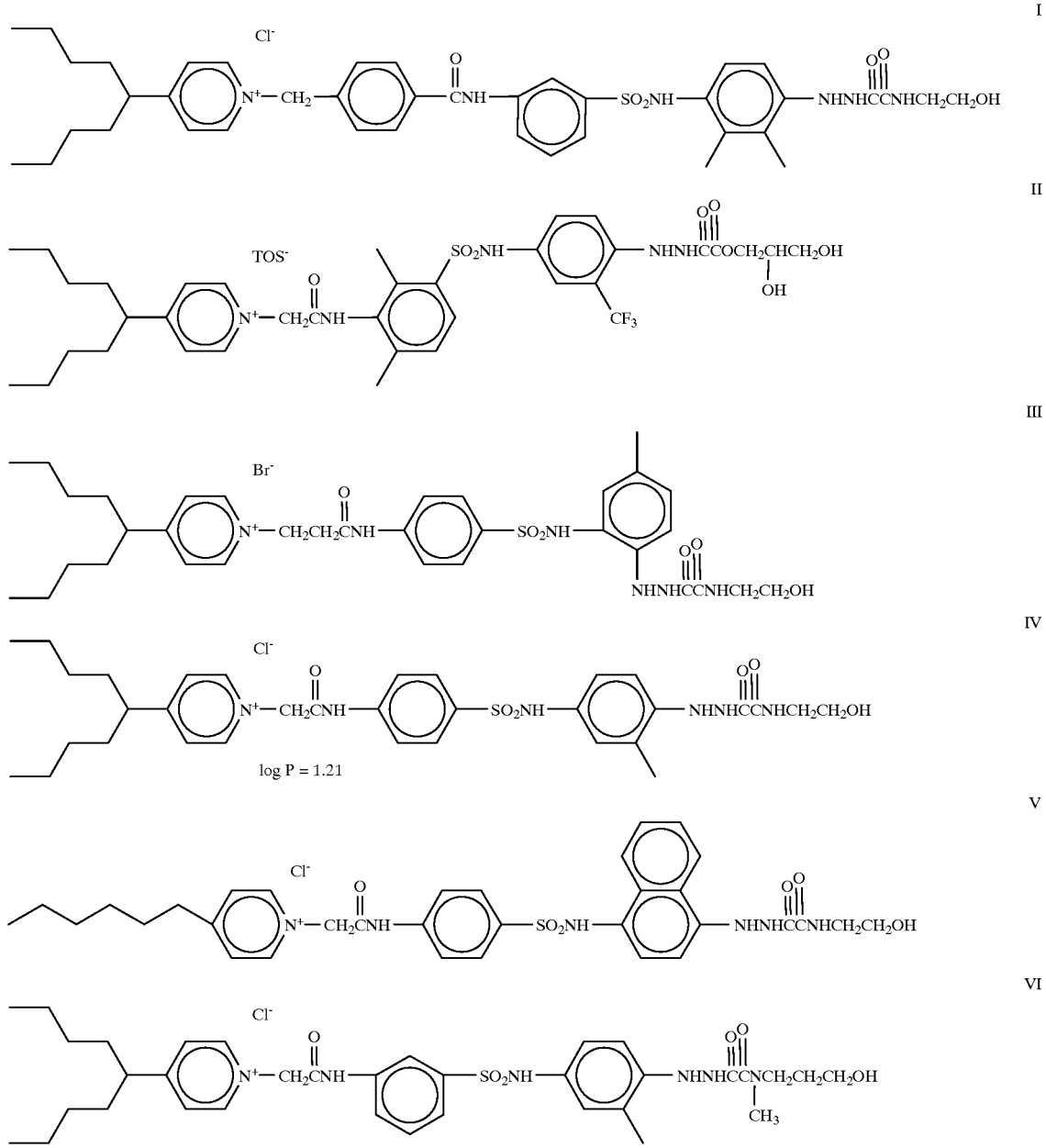

-continued
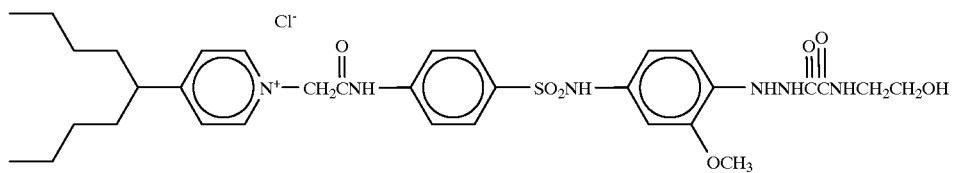
VII
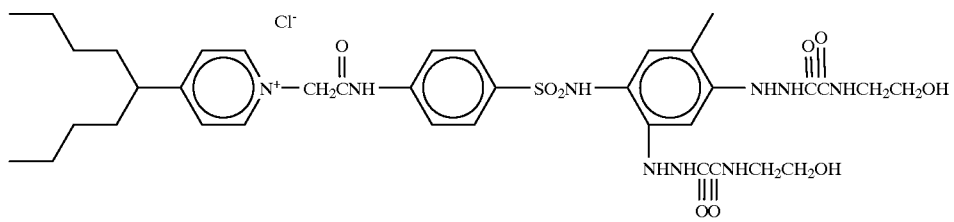
VIII
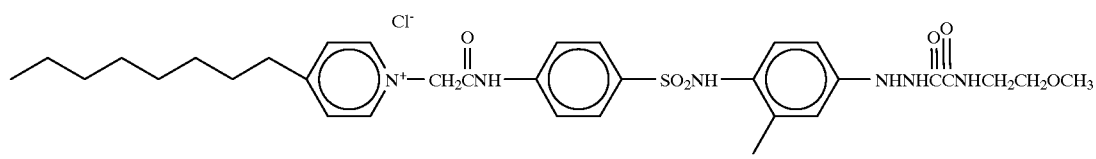
IX
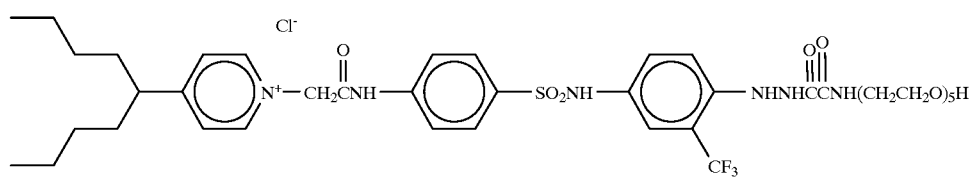
X
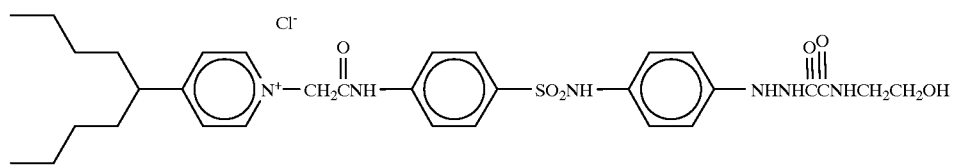
XI
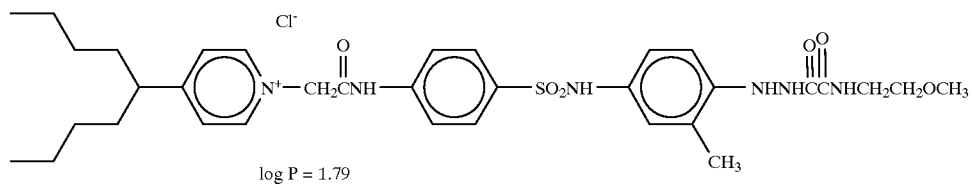
XII
log P = 1.79
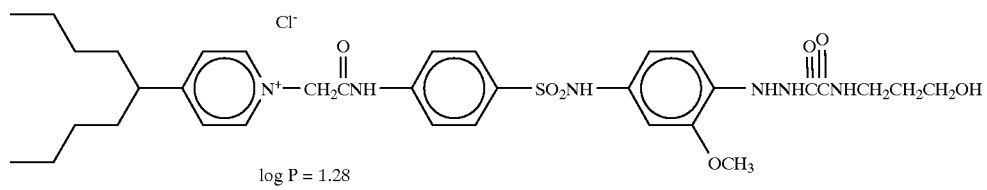
XIII
log P = 1.28
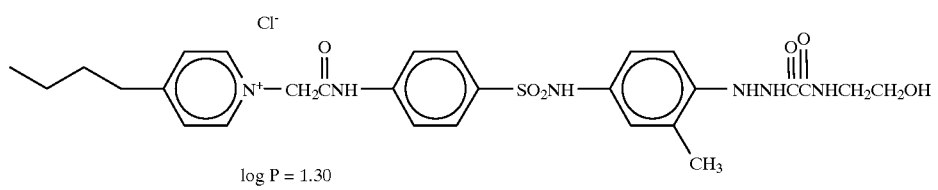
XIV
log P = 1.30

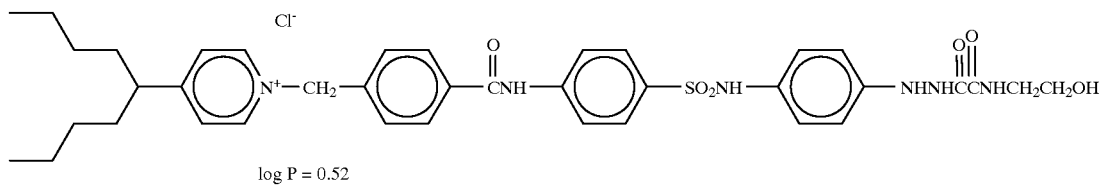

XV log P = 0.52

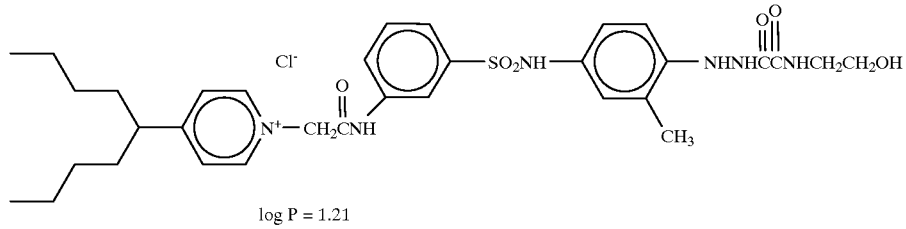

XVI log P = 1.21

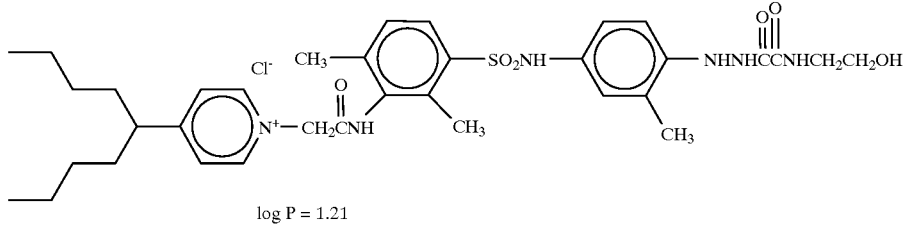

XVII log P = 1.21

In a preferred embodiment $R^1$ is lower alkyl, most preferably methyl, $R^2$ is hydrogen or lower alkyl, most preferably hydrogen, L is $NR^2$, Z is $C_2$–$C_6$alkyl substituted with an hydroxy group, most preferably hydroxy ethyl, $R^3$ is an alkyl group having from about 6 to about 10 carbon atoms, the Y group is phenyl or naphthyl, only one of A or B is —NHNH—COCO—L—Z, most preferably the A-group will be —NHNH—COCO—L—Z and B will be hydrogen, n is from 1 to about 3, and m is 0. Examples of preferred compounds of the invention include compounds IV, XII, XIII, XIV, XV, XVI, and XVII.

GENERAL SYNTHESIS:

The compounds of the invention can be synthesized according to the methods described in the literature, particularly U.S. Pat. No. 4,994,365. The synthesis of the hydrazides containing an hydroxyethylamido-oxalyl group are prepared as described in Scheme I, below. The amides and ester derivatives of the oxalic acid hydrazides can also be prepared by the methods described in Resnick et al., U.S. Pat. No. 4,686,167. In the present application, Intermediate D is equivalent to Intermediate IV in the 4,686,167 patent. Intermediate D can be converted to the corresponding hydrazide following the steps shown in Scheme I. The specific examples of compounds represented by Formula I, illustrated above, can be prepared using the route described in Scheme I by substituting reagents having appropriate groups for those illustrated or by other methods known to those skilled in the art.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835–9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds (including starting materials) which are not commercially available can be prepared by employing known methods from the chemical literature.

SCHEME I

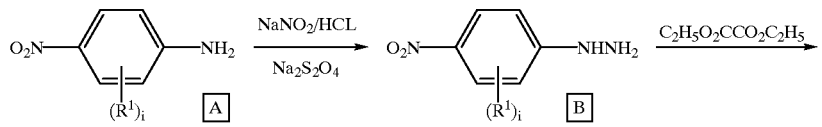

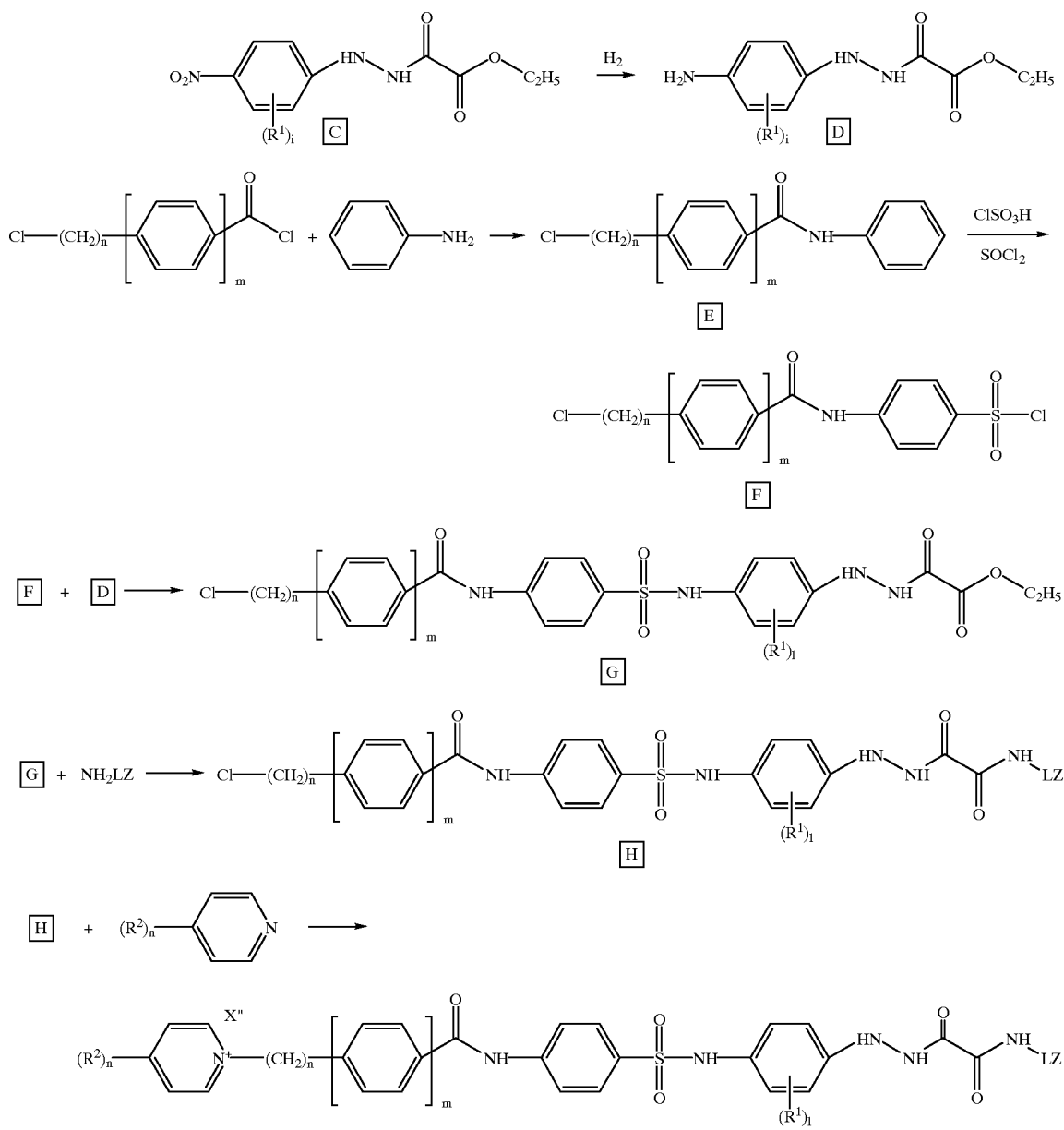

The amount of the compound of formula 1 added to the silver halide emulsion layer or to another hydrophilic colloid layer(s) of a photographic material is such that the compound does not appreciably function as a developer. Typically, amounts from $10^{-8}$ to $5 \times 10^{-2}$ moles/mole silver (Ag) and preferably about $10^{-6}$ to $10^{-3}$ moles/mole Ag are used.

The compound can be incorporated in a silver halide emulsion used in the photographic element. Alternatively, the hydrazide compound can be present in a hydrophilic colloid layer of the photographic element, preferably a hydrophilic colloid layer which is coated to be contiguously adjacent to the emulsion layer in which the effects of the compound are desired. The compound of the present invention can, of course, be present in the photographic element distributed between or among the emulsion and hydrophilic colloid layer(s), such as undercoating layers and overcoating layers. Methods for preparing the photographic elements are disclosed in U.S. patent application Ser. No.: 08/342,207, filed; Nov. 18, 1994; and U.S. patent application Ser. No.: 08/343,752, filed; Nov. 22, 1994.

The hydrazide compounds of the present invention are employed in combination with negative-working photographic emulsions comprising radiation-sensitive silver halide grains capable of forming a surface latent image, and a binder. The silver halide emulsions include the high chloride, chlorobromo or chlorobromoiodo emulsions conventionally employed in forming lith photographic elements as well as silver bromide and silver bromoiodide emulsions, which are recognized in the art to be capable of attaining higher photographic speeds. Generally, the iodide content of the silver halide emulsions is less than about 10 mole percent silver iodide, based on the total amount of silver halide.

The compound of Formula I can be incorporated in the photographic element by common techniques used for the addition of additives to photographic emulsions. The compound is typically dissolved in a solvent selected from water or organic solvents compatible with water, such as alcohols, glycols, ketones, esters, amides, and the like which exert no adverse influences on the photographic characteristics. Then the solution is added to the photographic element. Preferred solvents include dimethylformamide (DMF), dimethylsulfoxide (DMSO), N-methyl-2-pyrrolidinone (NMP) or water. Ultrasound can be employed to dissolve or suspend marginally soluble hydrazides.

The photographic light-sensitive material of this invention can be photographically processed using known methods and known processing solutions. The processing temperature usually ranges from about 18° to about 50° C., but temperatures lower than about 18° C. or higher than about 50° C. may be used. This invention is useful for the formation of an image by development in which a silver image is formed (a black-and-white photographic processing).

The developers used for black-and-white photographic processing preferably contain, as a developing agent, aminophenols (such as N-methyl-p-aminophenol), 3-pyrazolidones (such as 1-phenyl-3-pyrazolidone), dihydroxybenzene (such as hydroquinone) and other of the aforementioned developing agents. Specific examples of the useful developing agents include hydroquinone alone, hydroquinone plus N-methyl-p-aminophenol, hydroquinone plus 1-phenyl-3-pyrazolidones, and hydroquinone plus N-methyl-p-aminophenyl plus 1-phenyl-3-pyrazolidones. Also developing agents such as reductones and ascorbates usually together with an auxiliary developing agent of the 1-phenyl-3-pyrazolidone type may be used. Moreover, the developers usually contain an antioxidant, an alkali agent, a pH buffer or the like and, if desired, a dissolving aid, a color toning agent, a development accelerator, a surface active agent, an anti-foaming agent, a water softener, a hardener, a tackifier, etc. An anti-fogging agent (such as an alkali metal halide or benzotriazole) may be present in the developer.

According to this invention, even when development is carried out using a developer containing more than about 0.15 mol/l of sulfite ions, a gamma of more than 8 can be obtained. The pH of the developer is preferably between about 10.0 and about 11.5 and more preferably between about 10 and about 11.

Fixing solutions having a composition generally employed in the art can be used in the present invention. Not only thiosulfates and thiocyanates but also organic sulfur compounds known as fixing agents can be used as fixing agents in the present invention.

Preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thio-1,5-pentanediol, 3,6-dithio-1,8-octanediol, 9-oxo-3,6,12,15-tetrathio-1,17-heptadecanediol, etc., water soluble sulfur-containing organic dibasic acids and water-soluble salts thereof such as 2,2-ethylenebis-thioglycollic acid and the sodium salt thereof, etc., imidazolidinethiones such as methylimidazolidinethione, etc. These agents have been described in L. F. A. Mason, Photographic Processing Chemistry, pages 187 and 188, Focal Press (1966).

EXAMPLES

The invention will now be illustrated in the following examples which are illustrative of the invention but are not intended to limit the scope of the invention.

Example 1

STEP 1: Acetic Acid, ((2-hydroxyethyl) amino)oxo-,2-(2-methyl-4-nitrophenyl)hydrazide, (Intermediate 1)

2-Methyl-2-nitroaniline (30.8 g; 0.0202 mol) is suspended in a mixture of concentrated HCL (85 mL) and water (80 mL). The mixture is cooled to 5° C. and stirred for 0.5 hr. A solution of sodium nitrite (15 g; 0.217) in water (40 mL) is added at a rate to maintain the reaction temperature below 10° C. After addition, stirring is continued for 1 hr and the resulting solution is filtered and added at 10° C. to a solution of ascorbic acid (35.2 g; 0.20 mol) in water (20 mL). After stirring for 1 hr the yellow solid is filtered and suspended in methanol (300 mL). Ethanolamine (61 g, 1.0 mol) is added to the methanolic suspension. A red solution is obtained, and an orange precipitate is formed. Stirring is continued overnight. Acetic acid (60 g; 1.0 mol) is slowly added to make the mixture is slightly acidic, pH 5. The precipitate is filtered off, suspended in methanol (100 mL), filtered and dried in a vacuum oven at 50° C. The product is a yellow powder, yield: 43.4 g (77%).

STEP 2: Synthesis of Acetic acid,((2-hydroxyethyl) amino) oxo-2-(4-amino-2-methylphenyl)hydrazide, (Intermediate 2)

Intermediate 1 (2.24 g; 0.072 mol) is suspended in a mixture of methanol (100 mL) and NMP (100 mL) and 10% Pd/C (2.15 g) slurried in water (2–3 mL) is added. The mixture is pressurized with hydrogen at 100 psi. After the uptake of hydrogen, the catalyst is filtered off. The solution is then added to toluene. After 1 hour of stirring at 0° C. the yellow precipitate is filtered off and dried overnight in a vacuum oven at 50° C. The product is a light yellow powder, yield: 1.419 g (78%).

STEP 3: Synthesis of 4-((Chloroacetyl)amino) benzenesulfonyl chloride, (Intermediate 3)

Chloroacetanilide (4.53 g) is slowly added to chlorosulfonic acid (7.5 mL) at a temperature of 5° C. The solution is heated to 65° C. and thionyl chloride (0.78 mL) is added. After 10 minutes of gas evolution the reaction was cooled to room temperature. The mixture is added to ice/water (2.14 g/3.2 mL) and stirred for 30 minutes. The product was filtered, washed with water (60 mL), placed under vacuum at 50° C. and dried to a constant weight. The product is a white powder, yield: 4.81 g (67%).

STEP 4: Acetic acid, ((2-hydroxyethyl)amino)oxo-2-(4(((4-((chloroacetyl)-amino)phenyl)sulfonyl)amino)-2-methylphenyl) hydrazide, (Intermediate 4)

To a solution of Intermediate 2 (1.73 g; 6.9 mmol) in dimethylacetamide (5 mL) is added to a solution Intermediate 3 (2.02 g; 7.5 mmol). The mixture is heated and stirred at about 60° C. for 2 hours. After the reaction is cooled to room temperature a fine beige precipitate forms gradually. The precipitate is filtered off, suspended and washed in water (50 mL), filtered and dried in a vacuum oven at 40° C., to a constant weight. The amount of product obtained is 2.29 g (69% yield ).

STEP 5: Pyridinium,4-(1-butylpentyl)-1-(2((4-(((4-(2-((2-hydroxy-ethyl)amino)oxoacetyl)hydrazino)-3-methylphenyl) amino)sulfonyl)phenyl)amino)-2-oxoethyl)-chloride, (Formula IV)

4-(1-butylpentyl)pyridine (2.05 g) is added to a solution of Intermediate 4 (5.0 g) in Dimethylacetamide (15 mL) and heated to 80° C. for three hours. The mixture is cooled to room temperature and added to ethyl acetate (300 ml). The precipitate is filtered off and dried in a vacuum oven to give a light-orange powder.

Example 2

The emulsion used is a monodispersed cubic AgClBr (70 mole % chloride) type with an area equivalent diameter of 0.2 μm. It is internally rhodium doped with sodium hexachlororhodate at 0.109 ppm rhodium based on silver. The emulsion is coated at 3.6 g Ag/M² on a polyester base. Gelatin content is 2.85 g/m² with 0.61 g/m² latex (a polyacrylate with sulfate, hydroxyl and carboxyl groups). The emulsion is sulfur and gold ripened and sensitized with 3-ethyl-2[3-(3'-ethyl-2-(4,5-disubstituted benzothiazolinylidene)-1-propenyl]-4,5-disubstituted benzothiazolium iodide (44.29 mg/mole Ag) and 2-([5,5-dimethyl-3-((5-(3-substituted-thioxo-4-thiazolidinonyl)) ethylidenyi)-2-cyclohexen-1-ylidene]methyl)-3-substituted benzothiazolium salt (17.59 mg/mole Ag). The pAg is adjusted with NaCl and the emulsion is stabilized with triazaindolizine and phenylmercaptoterazole. The emulsion layer is overcoated with a gelatin layer containing a silica matting agent, hydroquinone, Dimezon S, sodium metabisulfate, a slippage agent and coating aid. The hydrazide is added to the emulsion (or adjacent layer) as a DMF/water solution at a level of 3 mmol/mole of silver.

The coated film samples were exposed on an Aerodyne Microsecond Laser Sensitometer, with a laser wavelength of 633 nanometers and having a beamwidth of 50 microns. The exposure was a series of adjacent parallel lines with a center-to center stepover spacing of 62 microns. The laser light was modulated by a step wedge of 21 steps each of 0.075 density units increments.

The exposed film was processed in a Polychrome processor at 35° C. for 35 seconds in a developer of the following composition:

| INGREDIENT | AMOUNT | |
|---|---|---|
| Deionized water | 560 | cc |
| 50% Aqueous Potassium hydroxide solution | 50.3 | cc |

| INGREDIENT | AMOUNT | |
|---|---|---|
| Diethylenetriamine pentaacetic acid | 2.4 | gm |
| Potassium metabisulfite | 50.3 | gm |
| Sodium sulfite, anhydrous | 11 | gm |
| Potassium carbonate | 28 | gm |
| Hydroquinone | 24.3 | gm |
| 4-Hydroxymethyl-4-methyl-1-phenyl-3-pyrazolidinone | 0.80 | gm |
| Diethylene glycol | 20 | cc |
| Benzotriazole | 0.20 | gm |
| 1-Phenyl-5-mercaptotetrazole | 0.027 | gm |
| Sodium bromide | 3.77 | gm |
| Deionized water to make total volume | 1000 | cc. |

The above concentrate is diluted with two equal parts of water to obtain a working developer solution with a working pH of 10.4. After fixing, washing and drying the strips were read on a Macbeth TR927 densitometer through a 3 mm aperture with light filtered to visual.

After development the material was fixed with a conventional fixing solution, washed with water and dried.

Example 3

In the examples that follow, a comparison is made between the preferred hydrazide of the present invention and structurally related hydrazides. An emulsion is prepared using the procedure described above with an emulsion using hydrazides having Formula 3, described in Table 1. The film is exposed and developed as described in Example 2. The films are evaluated for speed, screen range, line edge, and pepper.

The compounds tested have the following general structure:

Formula 3

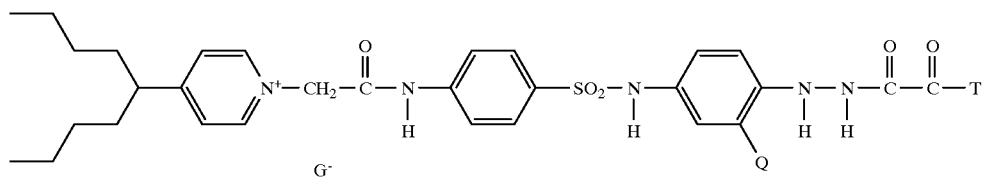

where Q and T are as shown in Table 1 and G⁻ is a chloride ion.

The results from the tests using inventive compounds IV and XI and comparative compounds 3 and 4 are in Table 1.

TABLE 1

| HYDRAZIDE COMPOUND | Q | T | HYDRAZIDE AMOUNT mmol/mol Ag | SHOULDER SPEED[2] | SCREEN RANGE[3] | LINE EDGE[4] | PEPPER[5] | LOG P |
|---|---|---|---|---|---|---|---|---|
| IV | methyl (-CH₃) | ethanolamine (-NHCH₂CH₂OH) | 0.16 | 110 | 0.52 | 2 | 1 | 1.21 |
| | | | 0.20 | 129 | 0.51 | 1 | 2 | |
| | | | 0.23 | 123 | 0.51 | 1 | 1 | |
| | | | 0.29 | 145 | 0.47 | 1 | 2 | |
| | | | 0.51 | 155 | 0.51 | 1 | 30 | |
| XI | hydrogen | ethanolamine (-NHCH₂CH₂OH) | 0.16 | 112 | 0.52 | 1 | 3 | 0.72 |
| | | | 0.20 | 129 | 0.49 | 1 | 0 | |
| | | | 0.23 | 148 | 0.46 | 1 | 1 | |
| | | | 0.29 | 145 | 0.47 | 1 | 1 | |
| | | | 0.51 | 186 | 0.44 | 1 | 80 | |

TABLE 1-continued

| HYDRAZIDE COMPOUND | Q | T | HYDRAZIDE AMOUNT mmol/mol Ag | SHOULDER SPEED[2] | SCREEN RANGE[3] | LINE EDGE[4] | PEPPER[5] | LOG P |
|---|---|---|---|---|---|---|---|---|
| 3 comp.[1] | methyl (–CH₃) | ethylamine (–NHCH₂CH₃) | 0.16 | 74 | 0.57 | 4 | 0 | 3.2 |
|  |  |  | 0.20 | 74 | 0.57 | 3 | 0 |  |
|  |  |  | 0.23 | 76 | 0.53 | 3 | 0 |  |
|  |  |  | 0.29 | 100 | 0.54 | 3 | 3 |  |
|  |  |  | 0.51 | 112 | 0.52 | 1 | 3 |  |
| 4 comp.[6] | hydrogen | ethylamine (–NHCH₂CH₃) | 0.16 | 78 | 0.55 | 4 | 0 | 2.7 |
|  |  |  | 0.20 | 96 | 0.53 | 4 | 0 |  |
|  |  |  | 0.23 | 100 | 0.51 | 2 | 0 |  |
|  |  |  | 0.29 | 107 | 0.50 | 1 | 0 |  |
|  |  |  | 0.51 | 138 | 0.48 | 1 | 2 |  |

1.) Comparative example compound.
2.) The speed reported is based on 100 and reported relative to the speed of Compound 4 at a hydrazide level of 0.23 mmol/mol Ag.
3.) The Screen Range, simulated, is determined ae described below.
4.) Line edge is evaluated at 50x magnification. A rating of "1" is acceptable for use while ratings of "2" to "4" indicate fuzzier line edges.
5.) Pepper is evaluated at 50x magnification. The average count in 5 fields is given. The field size is 2.5 mm². An average count of greater than 6 is rejectable.
6.) Compound Disclosed in U.S. Patent 4,994,365.

The speed reported is relative, based on the speed (100) of Compound 4 at a hydrazide level of 0.23 mmol/mol Ag. The line edge is evaluated at 50x magnification. A rating of "1" is acceptable for use while ratings of "2" to "4" indicate fuzzier line edges. Pepper is evaluated at 50x magnification. Strips were clear processed for 35 sec at 95° F. The average count in 5 fields is given. The field size is 2.5 mm. An average count of greater than 6 is rejectable.

SIMULATED SCREEN RANGE

The screen range was determined in the following manner. A test pattern is generated by the imagesetter where areas of the film are exposed with a pattern of dots increasing in 1% dot increments from file values of 1% to 100%. The screen range is taken as the difference in file values where all the dots are printable in both the highlight and shadow areas. (Screen range is determined on HDP 600 line screen 140 dots/mm exposures on a Dolev 200® (Scitex, Israel) imagesetter.) It has been found that this can be simulated using the following method:

Coated film samples were exposed on an Aerodyne Microsecond Laser Sensitometer. The exposure is made by a scanning HeNe (633 nanometer) laser beam making a raster pattern of parallel lines along the length of the film. (The nominal beam width is 50 microns while the center-to-center spacing between lines is 62 microns.) The laser light is modulated by a step wedge of 21 steps. Each successive step increases the light transmitted by ¼ stop. The steps are perpendicular to the direction of the exposing beam. At low exposures (higher step wedge density) the exposure pattern is seen as a series of lines. As the exposure increases (lower step wedge density) the exposure pattern fills in creating a uniform exposure.

After exposure and development of a sample film, the simulated screen range, reported in Table 1, can be determined. The difference in the log of the exposure required to produce an optical density of 0.06 minus the log of the exposure required to produce an optical density of 1.25 correlates with the actual screen range. The optical densities are measured on a densitometer and both densities are measured above "fog".

The data in Table 1 illustrate the effectiveness of the compounds of the subject invention when compared to comparison compounds. Compound 4 was disclosed in U.S. Pat. No. 4,994,365. The data show that preferred compound IV had a markedly better shoulder speed than prior art comparative compound 4 and comparative compound 3. Additionally inventive compound IV had a somewhat better screen range than compound XI and comparable to that of compound 4. Finally inventive compounds IV and XI had a much better line edge characteristics than either compound 3 or compound 4. All compounds had good pepper characteristics (except at certain high concentration, as indicated).

The invention has been described above by reference to preferred embodiments but, as those skilled in the art will appreciate, many additions, omissions and modifications are possible all within the scope of the claims below.

We claim:

1. A hydrazide compound having the formula:

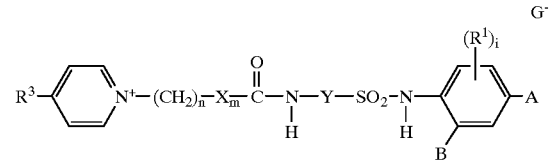

wherein each $R^1$ is independently selected from the group consisting of alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; or two of the $R^1$ groups taken together can form a carbocyclic ring containing 6–10 atoms;

wherein i is from 1 to 3, m is 1, and n is from 1 to about 6; A and B are independently selected from the group consisting of —NHNH—COCO—L—Z, hydrogen, alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; with the proviso that at least one of A and B is a —NHNH—COCO—L—Z group;

L is O, or $NR^2$;

$R^2$ is hydrogen, alkyl, or aralkyl; and

Z is selected from the group consisting of $C_2$–$C_6$alkyl and $C_3$–$C_6$cycloalkyl; wherein the alkyl and cycloalkyl groups are substituted with from 1 to 3 groups selected from hydroxyl, $C_1$–$C_3$hydroxyalkyl, $C_1$–$C_5$ alkoxy, polyethyleneoxy, and any combination of the foregoing;

$R^3$ is alkyl having from about 4 to about 20 carbon atoms or aralkyl having from 6 to about 10 atoms;

X and Y are substituted or unsubstituted aryl groups; and

G is a monovalent anion.

2. The hydrazide according to claim 1, wherein A is —NHNH—COCO—L—Z and B is hydrogen.

3. The hydrazide according to claim 1, wherein each $R^1$, is independently selected from the group consisting of lower alkyl, lower alkenyl, and alkoxy; or two of the $R^1$ groups taken together can form a carbocyclic ring containing 6–10 atoms.

4. The hydrazide according to claim 3, wherein each $R^1$, is independently selected from the group consisting of lower alkyl, lower alkenyl, and alkoxy.

5. The hydrazide according to claim 1, wherein L is $NR^2$; and $R^2$ is hydrogen, or lower alkyl.

6. The hydrazide according to claim 1, wherein G is selected from the group consisting of bromide, chloride, thiocyanate, tosylate and mesylate.

7. The hydrazide according to claim 6, wherein G is selected from the group consisting of bromide, chloride, and tosylate.

8. The hydrazide according to claim 1, wherein $R^3$ is selected from the group consisting of butyl, octyl, nonyl, and decyl.

9. The hydrazide according to claim 1, wherein Z is selected from the group consisting of $C_2$–$C_6$alkyl substituted with from 1 to 3 groups selected from hydroxyl, $C_1$–$C_3$hydroxyalkyl, $C_1$–$C_5$ alkoxy.

10. The hydrazide according to claim 1, wherein Y is phenyl naphthyl or tetrahydronaphthyl.

11. The hydrazide according to claim 1, wherein $R^1$ is lower alkyl, L is $NR^2$, $R^2$ is hydrogen or lower alkyl, Z is $C_2$–$C_6$ alkyl substituted with an hydroxy group, $R^3$ is an alkyl group having from about 6 to about 10 carbon atoms, the Y group is phenyl or napthyl, only one of A or B is —NHNH—COCO—L—Z, and n is from 1 to about 3.

12. The hydrazide according to claim 1, wherein $R^1$ is methyl, A is —NHNH—COCO—L—Z, B is hydrogen, L is $NR^2$, $R^2$ is hydrogen, Z is hydroxy ethyl, $R^3$ is nonyl, Y is phenyl, and n is 1.

13. The hydrazide according to claim 1, wherein the hydrophilic lipophilic balance is less than 2.2.

14. A photographic silver halide material which comprises in at least one layer thereof, at least one hydrazide according to claim 1.

15. The photographic silver halide material according to claim 14, wherein the hydrazide has formula I, wherein $R^1$ is lower alkyl, L is $NR^2$, $R^2$ is hydrogen or lower alkyl, Z is $C_2$–$C_6$alkyl substituted with an hydroxy group, $R^3$ is an alkyl group having from about to about 10 carbon atoms, the Y group is phenyl or naphthyl, only one of A or B is —NHNH—COCO—L—Z, n is from 1 to about 3, and m is 0.

16. The photographic silver halide material according to claim 15, wherein $R^1$ is methyl, A is —NHNH—COCO—L—Z, B is hydrogen, L is $NR^2$, $R^2$ is hydrogen, Z is hydroxy ethyl, $R^3$ is nonyl, Y is phenyl, n is 1, and m is 0.

17. A hydrazide compound having the formula:

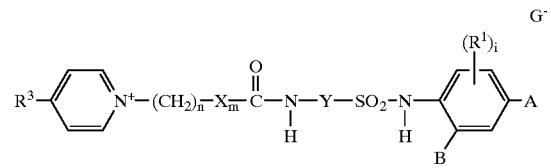

wherein each $R^1$ is independently selected from the group consisting of alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; or two of the $R^1$ groups taken together can form a carbocyclic ring containing 6–10 atoms;

wherein i is from 1 to 3, m is from 0 to 1, and n is from 1 to about 6;

A and B are independently selected from the group consisting of —NHNH—COCO—L—Z, hydrogen, alkyl, alkenyl, alkynyl, aralkyl, cycloalkyl, cycloalkenyl, haloalkyl, hydroxyalkyl, alkoxy, thioalkyl, aryloxy, acyloxy, alkylsulfonylamino, arylsulfonylamino, and acylamino; with the proviso that at least one of A and B is a —NHNH—COCO—L—Z group;

L is O, or $NR^2$;

$R^2$ is hydrogen, alkyl, or aralkyl; and

Z is selected from the group consisting of $C_2$–$C_6$alkyl and $C_3$–$C_6$cycloalkyl;

wherein the alkyl and cycloalkyl groups are substituted with from 1 to 3 groups selected from hydroxyl, $C_1$–$C_3$hydroxyalkyl, $C_1$–$C_5$ alkoxy, polyethyleneoxy, and any combination of the foregoing;

$R^3$ is aralkyl having from 6 to about 10 atoms;

X and Y are substituted or unsubstituted aryl groups; and

G is a monovalent anion.

* * * * *